(12) United States Patent
Martin

(10) Patent No.: US 6,270,343 B1
(45) Date of Patent: Aug. 7, 2001

(54) ENDODONTIC THERMAL CONDENSER DENTAL INSTRUMENT

(76) Inventor: Howard Martin, 11500 W. Hill Dr., Rockville, MD (US) 20852

( * ) Notice: Subject to any disclaimer, the term of this patent is extended or adjusted under 35 U.S.C. 154(b) by 0 days.

(21) Appl. No.: 09/479,099

(22) Filed: Jan. 7, 2000

(51) Int. Cl.[7] .................................................. A61C 3/00
(52) U.S. Cl. ................................................................ 433/32
(58) Field of Search ..................................... 433/32, 224

(56) References Cited

U.S. PATENT DOCUMENTS

| | | |
|---|---|---|
| 3,899,830 * | 8/1975 | Malmin . |
| 4,265,618 * | 5/1981 | Herskovitz et al. ............... 433/32 |
| 4,392,827 * | 7/1983 | Martin ................................ 433/32 |
| 4,527,560 * | 7/1985 | Masreliez ........................... 433/32 |
| 4,992,045 * | 2/1991 | Beisel ................................. 433/32 |
| 5,043,560 * | 8/1991 | Masreliez . |
| 6,106,283 * | 8/2000 | Roffe et al. ........................ 433/32 |

* cited by examiner

Primary Examiner—Ralph A. Lewis
(74) Attorney, Agent, or Firm—Law Offices of Royal W. Craig

(57) ABSTRACT

A self-contained root canal dental instrument that combines the operations of a root canal spreader, a root canal condenser, and a root canal filling material heater in a less expensive and easier to replace plugger unit. A different heating circuit using balanced resistor elements in both the hand piece and the tip makes use of the instrument more cost effective for the dentist. The instrument combines a sterilizable condenser tip with the capability of achieving the correct heating temperature via standard AA alkaline batteries.

2 Claims, 3 Drawing Sheets

ENDODONTIC THERMAL CONDENSER DENTAL INSTRUMENT

BACKGROUND OF THE INVENTION

1. Field of the Invention

The present invention relates to dental treatment equipment and root canal dental instruments. Specifically, it relates to a self-contained root canal dental instrument that combines the operations of a root canal spreader, a root canal condenser, and a root canal filling material heater.

2. Description of the Background

A need has existed for a long time for a way to reduce the time involved in filling a prepared root canal of a human tooth with the filling material. The time involved being used in the continual pick up of separate dental tools for spreading filling material, condensing the filling material, and the alternate heating and reheating of the filling material, during the spreading and condensing operations. Equally important is the complete adaptation of the filling material to secure a hermetic seal against leakage.

Gutta percha is the usual material that is used for filling root canals. Gutta percha, as with other root canal filling materials, must be spread and condensed in the root canal and heated to improve its flow and adaptation qualities. Gutta percha material deforms when warmed and compressed. It becomes pliable at 25 to 30 degrees Celsius, it becomes soft at 60 degrees Celsius, and it decomposes at 100 degrees Celsius. At such temperatures a phase transition occurs allowing the gutta percha to flow into the many irregularities of the prepared root canal, thus allowing for a three-dimensional obturation and sealing to occur. Such a three-dimensional obturation and sealing is necessary for success in root canal therapy.

When the filling material is softened, it is then compressed into the numerous aberrations of the root canal in order to effectively seal the root canal cavity. The compressing of the filling material in the prior art is performed by using root canal filling spreaders and filling condensers of a variety of sizes and with several handle designs (both long and short). The root canal filling spreaders and filling condensers deform the filling material under heat and stress and allow compaction and condensation that leads to the lateral spreading to fill the voids in the root canal. As bits or points of filling material are placed into the root canal, as hereinbefore described, the heated, spreader tool is forced between the bits or points of material after each such insertion which pushes and compacts the filling material vertically to the apex of the root canal and, concurrently, laterally. The tool is pressed manually and also rotated side to side to achieve the spreading of the material. It also acts as a heat sink cooling down quickly for controlled concentration.

The filling spreaders and condensers of the prior art for root canal work are generally of stainless steel or chromium plated brass. The filling spreaders are smooth, flat ended and slightly tapered. For the most part, the prior root canal filling spreaders and condensers had to be heated over a flame, such as over the flame of a Bunsen burner, and then passed into the mouth of a dental patient and then into the prepared root canal where the filling material has been placed. Such tools had to be transported quickly from the Bunsen burner into the mouth of the patient and into the tooth and the root canal and against the cold mass of filling material. There is the constant danger of burning the patient about the mouth each time a heated dental tool is moved from the flame to inside the mouth. Moreover, if it becomes too hot the filling material will stick to the dental tools of the prior art.

A few prior art attempts have been made to provide for heating the tools while in the mouth. However, problems have been encountered. For example, the tips have been bulky and too wide. Also, the tips do not wedge lock into place and 360 degree rotation has been encountered which reduces the effectiveness of the condensing operation. Further, the heat control has been unreliable, the system having as many as ten dial settings which required an assistant or required the dentist to stop the condensing operations to attempt to make a better heat selection or to interrupt the heat process. In addition to the above problems, the filling material sticks to the surface of the so called heat control tools, and the system has a cumbersome power box and control means.

U.S. Pat. No. 4,392,827 issued Jul. 12, 1983 to the inventor herein proposes a solution in the form of a self-contained dental instrument inclusive of a combination spreader, condenser, and a filling material heating unit, each of which is alternately and/or concurrently useable while inserted within the root canal structure of a patient. The '827 invention generally includes a plugger component or "tip" which combines the functions of a spreader, a condenser, and a material heating unit; a handle component affixed to the plugger component; a power supply component for producing heat; and a transmission component for transmitting heat produced by the power supply component to the material heating unit of the plugger component. The transmission component has a conveniently located finger operation switch to interrupt the power supply and cut off the flow of heat. A variety of plugger components are provided in a range of sizes to fit the range of internal sizes in different parts of the root canal. The '827 invention reduces the number of entries into the mouth that are necessary during a root canal filling, and also provides for inducing the heat for the tool after the tool is in the tooth at the root canal cavity. The plugger unit or tip is used to heat the filling material and then laterally condense or press the filling material into the root canal areas. Thereafter, the tip may also be used to maintain the heat or reheat the filling material and to vertically condense the filling material into the root canal in a compacting type of operation. While the use of the filling condenser to vertically condense the filling material is often referred to as a plugging operation, the use of the filling spreader to laterally condense the material before the vertical condensing is is also a part of the total plugging operation. Additional bits or points of filling material are placed into the root canal cavity and then followed by the spreading and condensing operations described hereinbefore for the filling spreader and condenser root canal tools. These operations are continued until the required amount of filling material plugs and seals the root canal in accordance with dental art.

The above-described invention eliminates the risk and expense of the many repeated tool exchanges and reheating operations. However, the device itself has proven expensive. The '827 device made use of a tip which housed both heating element and resistor. The presence of the resistor within the tip increased the cost. More significantly, the tip could not be sterilized due to the resistor.

It would be greatly advantageous to provide a modified design in which the resistor is moved out of the tip and into the hand piece, along with other design modifications, to thereby make the instrument more cost effective for the dentist and sterilizable for infection control requirements.

SUMMARY OF THE INVENTION

It is, therefore, an object of the present invention to provide A self-contained root canal dental instrument that combines the operations of a root canal spreader, a root canal condenser, and a root canal filling material heater in a less expensive and easier to replace plugger unit.

It is another object to accomplish the foregoing by incorporating a heating resistor element in the hand piece rather than the condenser tip, thereby making the tip removable and sterilizable. This in turn satisfies the infection control requirements of the Food and Drug administration, and makes the use of the instrument much more convenient and cost effective for the dentist.

It is a necessary object to accomplish the foregoing by employing a different heating circuit within the hand piece, the heating circuit being adapted to provide a proper impedance (inclusive of parallel resistances, proper length and proper amounts of copper flashing) to allow correct heating within the tip.

It is a further object to provide an improved insulation system for the tip described above.

It is still another object to replace the NiCad batteries and recharger as suggested in U.S. Pat. No. 4,392,827 issued Jul. 12, 1983 to the inventor herein with conventional alkaline batteries, and to adapt the electronics and housing accordingly.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DESCRIPTION OF THE PREFERRED EMBODIMENTS

Gutta percha is a high molecular weight polymer trans polyiosprene. If it is heated above 65° C. it becomes amorphous. It is cooled at 0.5° C. per hour and will slowly recrystallize in the beta form which is the form of dental gutta percha usage. Gutta percha may be applied by the lateral condensation technique. This is a compression of solid gutta percha cones together and adaptation to the root canal walls.

Figure 1:
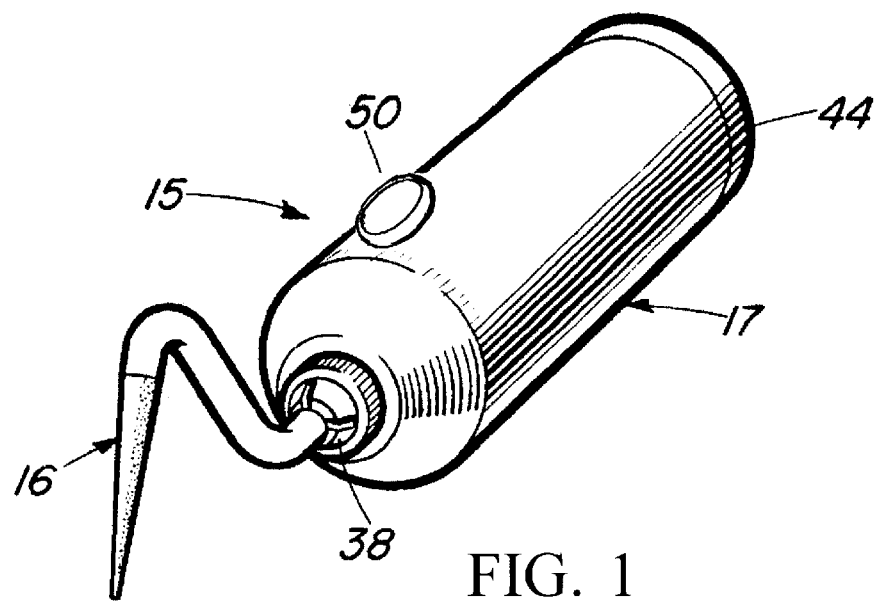
FIG. 1 is a pictorial view of a self-contained root canal heated condenser dental instrument according to the present invention.

Referring now to the drawings and particularly to FIG. 1, an improved self-contained root canal heated condenser dental instrument 15 is shown for practicing the lateral condensation technique. The instrument 15 of FIG. 1 includes a plugger component 16 and a handle component 17.

Figure 2:
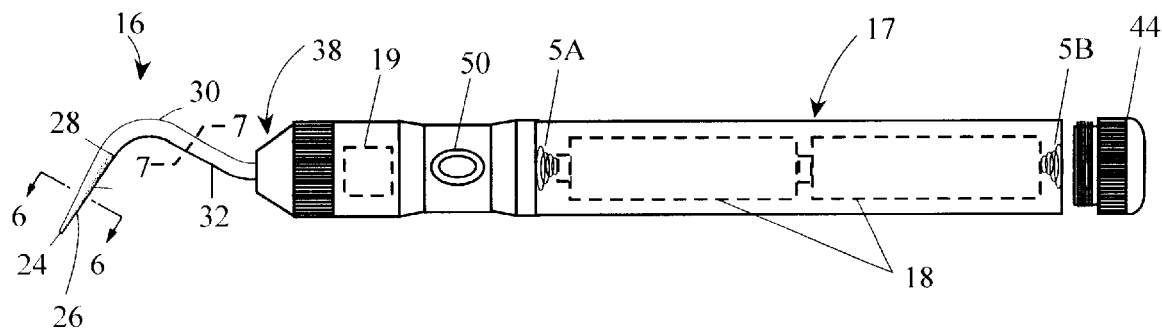
FIG. 2 is a side view of the instrument of FIG. 1.

FIG. 2 is a side view of the instrument 15 of FIG. 1 with internal components indicated by dotted lines. Inside the handle component 17 is a power source 18 and a heat transmission coupling 19. The structure of each of the plugger component 16, handle component 17, power source 18, and a coupling 19 for plugger component 16 as described hereinafter.

The power source 18 must be sufficient to provide the control heat as hereinafter described. Preferably, the power source 18 comprises a pair of standard alkaline AA batteries that fit inside the end of the handle component 17 at the distal end from the plugger component 16. A screw-on end closure 44 with terminal spring 5A provides an easy access means for inserting the power source 18. When screw-on end closure 44 is installed, a conductive path exists from one output terminal of the power source 18 through terminal spring 5A and handle component 17 (via a conductive metal trace or a conductor wire housed therein). The instant use of ordinary alkaline batteries rather than NiCad batteries and recharger helps to keep the unit cost low.

Figure 3:
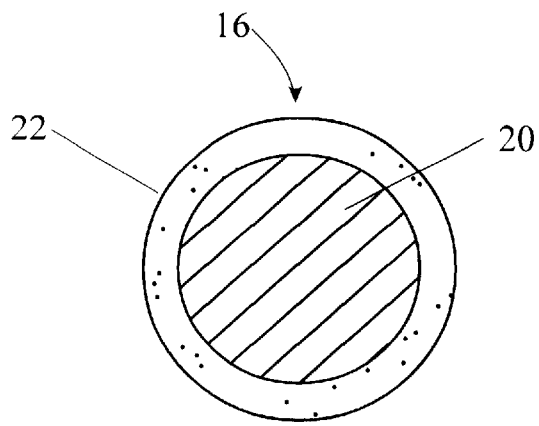
FIG. 3 is an enlarged cross sectional view on line 6—6 of FIG. 2.

The plugger component 16 is preferably formed as two pieces including a tapered tip 26 joined to an extended portion 30. The tapered tip 26 consists of a main resistive core 20 with a Teflon coating 22, both as shown in FIG. 3, which is an enlarged cross sectional view on line 6—6 of FIG. 2. Resistive core 20 may be formed of conventional ceramic resistor material.

Referring to FIG. 2, the Teflon coating 22 extends from the pointed end of tapered tip 26 to the top 28 of the tapered portion 26. The Teflon coating 22 covers both the end 24 of the core 20 as well as the tapered portion 26. The extended portion 30 is a more or less uniform diameter for the balance of the extension, as hereinafter described, to the an end that inserts into the heat transmission coupling 19. The extended portion 30 is bent in a convenient goose neck like configuration to a straight portion 32 that inserts into the aforementioned coupling 19. It is to be understood that the extended portion 30 may be maintained straight, bent at a right angle, or formed into any other configuration, and all such variations are within the scope and intent of the invention. The plugger component 16 includes tapered portion 26 (core 20 and the Teflon coating 22), as well as the extended portion 30 and straight portion 32.

Figure 4:
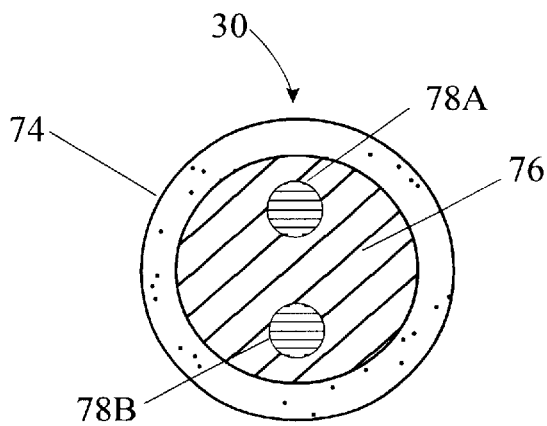
FIG. 4 is an enlarged cross sectional view on line 7—7 of FIG. 2.

FIG. 4 is an enlarged cross sectional view of the extended portion 30 of plugger component 16 along line 7—7 of FIG. 2. The extended portion 30 is insulated 74 about the periphery, as shown in FIG. 4. In addition, a central layer of insulation 76 separates two conductive leads 78a and 78b. The outer insulation 74, central layer of insulation 76, and conductive leads 78a and 78b run the entire extent of the extended portion 30 from the interface with the tapered portion 26 to a point 36 just clear of chuck 38. The outer insulation 74 is preferably a layer of Pyre-ML, which is an enamel used in the motor industry for coating electrical windings. The insulation 74 also provides protection against burning of parts of the mouth of a dental patient while root canal work is being done.

In accordance with the present invention, the tapered tip 26 is bonded to extended portion 30 at a junction 28 using Master Bond® Epoxy No. EP42Ht. This particular epoxy has been tested under a force gage at 50 lbs. until shearing took place. Thus, using the International standard for hypodermic needles ISO 7864, it has been determined that the tapered tip 26 can withstand an acceptable push-out force of at least 9.25 lbs. This bonding material also acts as a heat shield to confine the heat to the tapered portion 26 and to keep the extended portion cool. This is an important safety feature and it allows almost immediate cold compaction of the root canal filling material.

Figure 5:
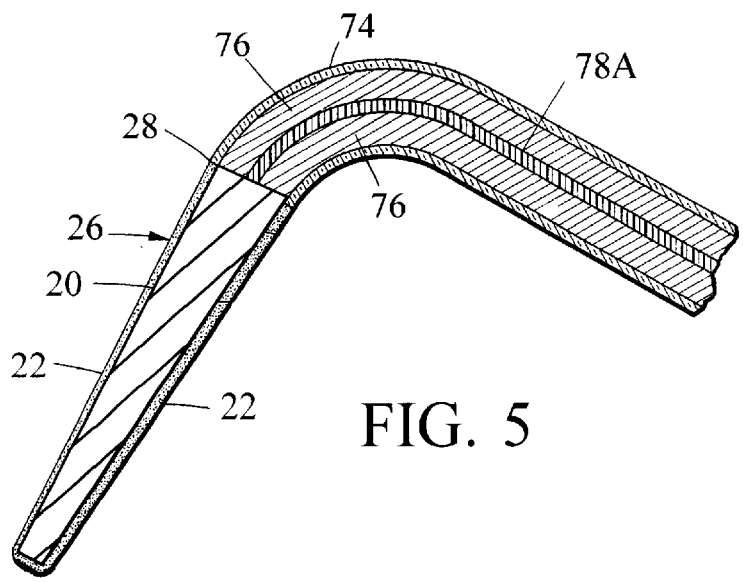
FIG. 5 is an enlarged side perspective view of the tapered tip 26 of plugger component 16.

FIG. 4 is a cross-section of the extended portion 30, and FIG. 5 is an enlarged side perspective view of the tapered tip 26 of plugger component 16, both showing the internal conductive leads 78a. Tapered tip 26 is bonded such that both conductive leads 78a and 78b make electrical contact with the resistive core 20 of the tapered portion 26. Heating at the tapered portion 26 is accomplished with the insulated lead 78a extending downward through the extended portion 30 to the tapered portion 26, and with identical return 78b. Both conductive leads 78a and 78b are insulated. This way, application of power from power source 18 through the conductive leads 78a and 78b and into the resistive core 20 generates heat therein which is quickly transmitted outward through the Teflon coating 22. The Teflon coating 22 prevents the root canal filling material from sticking or adhering to the plugger component 16 at the area of contact during a root canal treatment. The heat in the core 20 will readily pass through the Teflon coating 22 to heat the root canal filling material during treatment.

The extended portion 30 of plugger component 16 may be provided in a variety of sizes and shapes for use in root canal work that may vary from near the front of the mouth to the very back of the mouth. For example, a long neck exterior portion 40 facilitates reaching the back teeth.

Figure 6:
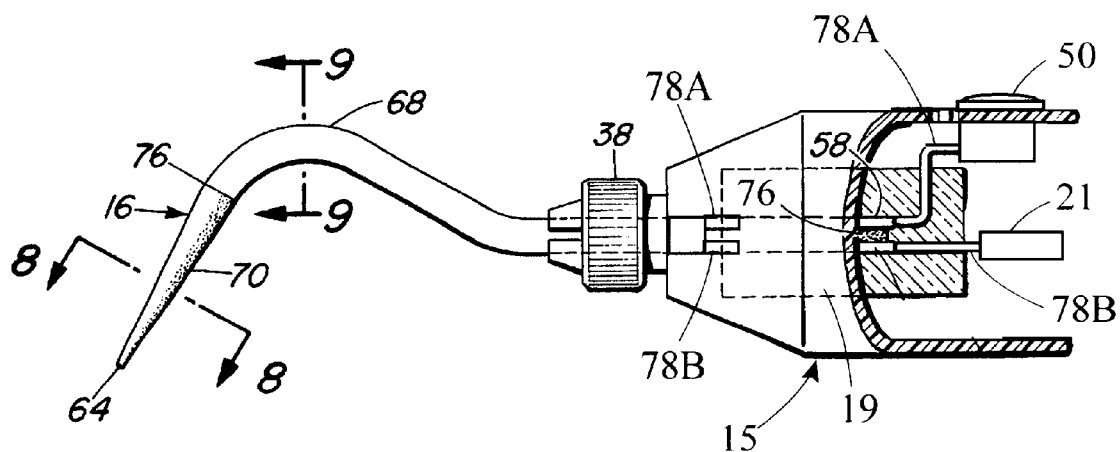
FIG. 6 is a side partial cut away view of the handle component 17 of dental instrument 15.

FIG. 6 is a partial cross-section showing the plugger component 16 coupled into the end of the handle component 17 with the conductive leads 78a and 78b extending into coupling 19. This is accomplished by inserting the plugger component 16 into the end of the handle with leads 78a and 78b inserted into mating receptacles in coupling 19, and then anchoring the plugger component 16 therein by screw-tightening a chuck 38. Once connected, one of the leads 78b completes an electrical circuit with power source 18 through a balance resistor 21 which allows control over the amount of heat dissipated by the plugger component 16. The other conductive lead 78a is connected to one terminal of switch 50. The combined conductive leads 78a and 78b essentially make a loop down to the end of the plugger component 16, starting as aforementioned at switch 50, running out through the extended portion of plugger component 16, around the gooseneck bend of the extended section 30, then down the tapered section 20, then back through the gooseneck bend of the extended section 30, through the straight section 66 and making the aforementioned contact with the opposite terminal of power source 18.

Figure 7:
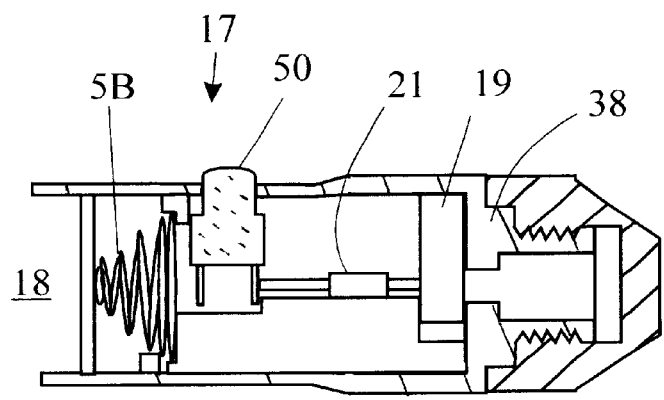
FIG. 7 is a side cross-section of the handle component 17 of dental instrument 15.

FIG. 7 is a cross-section of the handle component showing the chuck 38 for connecting and holding the plugger component 16 in place. The chuck 38 is affixed to the handle component 17 at an aperture in the handle component 17 through which the end of the plugger component 16 passes to insert into the heat transmission coupling 19. The handle component 17, in addition to serving as the means for a dentist to hold and use the root canal dental instrument 15 manually, also serves as a case or housing for the power source 18 and the heat transmission coupling 19. The chuck 38 is threaded onto the distal end of handle component 17, the tightening or which secures the plugger component 16 (not shown) in place.

The power source 18 aforementioned is biased at the leading end by another terminal spring 5B, terminal spring 5B also serving as a conductive path to a spacer switch 50. Depression of the spacer switch 50 further completes the conductive path to the heat transmission coupling 19 as hereinafter described. The switch 50 is preferably a push-button activator pad positioned for thumb operation at the neck of the instrument 15 and easily depressed while holding the root canal dental instrument 15 by the handle component 17. A variety of suitable switches are readily available for use as spacer switch 50. The spacer switch 50 is set in a normally "off" position and depressing it with the finger, as hereinbefore described, turns the switch "on" to provide power to the heat transmission coupling 19. The switch 50 is spring-loaded and it automatically returns to the "off" position when the finger is removed or lifted. The switch 50 is connected in series between the power source 18 via terminal spring 5B and through a conventional resistor 21, resistor 21 in turn being connected through the handle component 17 (either directly or by an internal conductor) to the opposite polarity terminal spring 5A. The resistor 21 is an integral part of the heat transmission coupling 19, such that when the end of the plugger component 16 is inserted into the heat transmission coupling 19, the resistance of resistor 21 is in series with that of tapered portion 16, and the two resistances are balanced to provide appropriate heating of the tip as desired. Thus, upon depression of spacer switch 50 approximately 3 volts of power is applied across the series-coupled heat-dissipating core 20 of tapered portion 16 and the resistor 21, and heat is generated thereby at the tip. The leads of resistor 21 and all other series conductors as necessary are preferably formed from nickel-chrome wire. A conventional 1.4 ohm resistor makes a suitable resistor 21. A layer of insulation encircles the immediate area around the resistor 21. The insulation is preferably a section of polyester shrink tubing with an average wall thickness of 0.00025 inches. Heat transmission coupling 19 is open at the other end to surround the straight portion 32 of the plugger component 16. The heat in the heated tapered portion 26 passes through the Teflon coating 22 for use in heating the root canal filling material, as hereinbefore described, so that the root canal dental work can be performed.

Given the above-described configuration, the heat in the heated tapered portion 26 has been found to vary between 150 to 250 degrees Fahrenheit. This is a higher heating capacity when compared to the device of the '827 patent. During clinical testing the heat resulted in thermo-softening of the gutta percha in approximately three seconds. Compacting was then easily accomplished to provide excellent results. Moreover, the utilization of standard AA batteries, and the placement of the resistor 21 inside the handle unit have greatly reduced the cost of the device. Further, inasmuch as the resistor 21 resides within the handle rather than the plugger component 16, the entire plugger component 16 can now be removed and sterilized. This is extremely important inasmuch as the Food and Drug administration and Occupational Safety and Health administration require adequate sterilization to control infection. In clinical testing the instrument 15 has been found to be easy to use, consistent in both heating and compaction, and generally improving of the quality of root canal fills.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. For example, the range of sizes of the plugger component 16 may provide the range of lengths of the exterior neck 40, as mentioned hereinbefore, and may also provide a range of diameters at the small end of the tapered portion 26. The range of these small end diameters may begin with a very small diameter of less than one-half millimeter that is measured over the end of the core 20 and its Teflon coating 22. It is to be understood, therefore, that the invention may be practiced otherwise than as specifically set forth in the appended claims.

I claim:

1. A self-contained root canal heated condenser dental instrument, comprising:

a hollow handle component for gripping and including a conductive path substantially from end to end;

a removable closure mountable at one end of said handle and having a first terminal therein for connection to said conductive path;

a battery power source seated inside the hollow of said handle and having a first terminal in contact with the first terminal of said closure;

a switch mounted on said handle for selectively applying a second terminal of said power source to a balance resistor located inside said handle;

a plugger component having a heat-dissipating resistive tip bonded to an extended portion and a pair of conductive leads internal to said extended portion and in contact with said tip, said plugger coPonent being insertable into another end of said handle such that said resistor makes electrical contact with one of said pair of conductive leads, and the other of said conductive leads completes a conductive circuit to said conductive path;

whereby upon depression of said switch power is applied through said pair of internal conductive leads to generate heat at the heat-dissipating tip for heating, spreading and condensing root canal filling material when filling root canal cavities.

2. The self-contained root canal heated condenser dental instrument according to claim 1, wherein said plugger component is a heat-resistant unitary member adapted for removal from said handle and sterilization.

* * * * *